United States Patent [19]

Fogel et al.

[11] Patent Number: 4,559,226

[45] Date of Patent: Dec. 17, 1985

[54] SELF-EMULSIFYING ALKOXYLATE ESTERS

[75] Inventors: Arnold W. Fogel, Park Ridge; Ronald J. Smith, Upper Montclair, both of N.J.

[73] Assignees: Bernel Chemical Company Inc., Tenafly; Heterene Chemical Company, Inc., Paterson, both of N.J.

[21] Appl. No.: 529,750

[22] Filed: Sep. 6, 1983

[51] Int. Cl.$^4$ .................. A61K 7/34; A61K 7/38; C07C 69/22; C07C 69/767

[52] U.S. Cl. .................. 424/66; 260/410.6; 424/68; 560/103; 560/128; 560/130

[58] Field of Search .................. 260/410.6; 424/65, 66, 424/67, 68; 560/103, 128, 130

[56] References Cited

U.S. PATENT DOCUMENTS

| | | | |
|---|---|---|---|
| 3,033,680 | 5/1962 | Milton et al. | 430/637 |
| 3,539,518 | 11/1970 | Feighner et al. | 252/174.21 |
| 4,229,432 | 10/1980 | Geria | 424/66 |

*Primary Examiner*—Natalie Trousof
*Assistant Examiner*—John T. Sullivan
*Attorney, Agent, or Firm*—Edward R. Weingram

[57] ABSTRACT

Novel self-emulsifying alkoxylate esters are described having a cloud point of less than about 15° C. the structural formula:

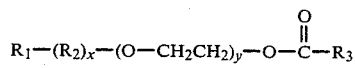

$R_1$ contains from 2 to 20 carbon atoms and is selected from the group consisting of aliphatic and aromatic substituents and $R_3$ is an alkyl or aryl substituent from 1 to 21 carbon atoms. One of $R_1$ and $R_3$ must contain greater than 8 carbon atoms.

$R_2$ is:

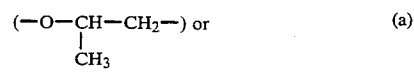

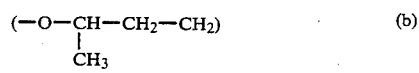

x is from 1 to 10 and y is from 1 to 20 and the ratio of y to x is from 2:1 to 10:1.

These alkoxylate esters are particularly useful in preventing the chalking of antiperspirant compositions containing volatile silicone oil by adding to the antiperspirant composition a chalking preventative amount of such ester. The compositions are also useful in a broad range of cosmetic compositions, and form stable oil-in-water emulsions at room temperature.

30 Claims, No Drawings

SELF-EMULSIFYING ALKOXYLATE ESTERS

BACKGROUND OF THE INVENTION

1. Field of the Invention

This invention relates to self-emulsifying alkoxylate esters which are particularly useful in preventing the chalking of anhydrous silicone oil containing antiperspirant compositions. The compounds may also be used in preparation of stable cosmetic oil-in-water emulsions by a "cold process". The compounds may also be used as the basis of a dispersible oil-system.

2. Prior Art

Previously in order to achieve stable oil-in-water emulsions, two phases, i.e. an oil phase and a water phase were heated separately to, for example 80° C., and mixed together under agitation and cooled to, for example 25° C., with agitation. Sometimes homogenization of this emulsion was required. Typically the oil phase in such a system comprised one or more fatty substances and one or more surfactants, any one of which may be solid. It has been sought in the art to eliminate the heating, agitation and homogenization steps, but with little success. It is also desirable to eliminate the need for a surfactant(s), (emulsifier).

Additionally, previously to make a water dispersible cosmetic oil, one or more oils would be blended with one or more surfactants, emulsifiers, dispersants or spreaders. Again, it would be desirable to eliminate such additives.

Still further, antiperspirants containing volatile silicone oil, for example DRY IDEA, from Gillette Co., Boston, Mass., typically show a white residue on the skin after application of the perspirant and drying. This is caused by the volatilization of the silicone oil which leaves behind the film of the non-volatile, powdering ingredients. Attempts have been made to solve this problem without destroying the efficacy of the active antiperspirant ingredient. To date, applicants are not aware of any practical solutions.

More specifically, detailed patentability searches were performed by Applicants herein and uncovered the following U.S. Patents: Nos.

1,739,315 to Kessler;
2,480,185 to Fife;
2,723,287 to Copenhaver;
2,755,296 to Kirkpatrick;
2,905,681 to Benneville;
2,950,310 to Kirkpatrick;
2,950,313 to Kirkpatrick;
2,962,341 to Cox;
3,033,680 to Milton;
3,365,402 to Brenkman;
3,391,228 to Nehmsmann;
3,488,370 to Leary;
3,539,518 to Feighner;
3,767,786 to MacMillan;
3,965,150 to Moeller;
3,974,270 to Kenkare;
4,022,808 to Yoshihara;
4,229,432 to Geria;
4,264,586 to Callingham; and British Pat. No. 1,156,812 to Farbwerke Hoeshst.

A review of all of these references discloses that none teach the herein claimed compositions nor teach the use of such compositions, or compositions similar thereto, for the prevention of chalking in antiperspirant compositions containing volatile silicone oil.

Specifically, Milton, which is perhaps one of the most relevant references, describes materials which are useful for plasticizing gelatin which have the formula:

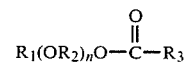

wherein, $R_1$ may be an alkyl, $R_2$ may be alkylene, and $R_3$ may be an alkyl, n may be a simple integer from 1 to 8. This formula does not teach or encompass the claimed alkoxylate esters.

Feighner, another relevant reference, describes a composition having the following formula:

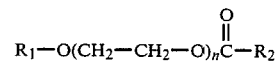

wherein, $R_1$ may be $C_4$ to $C_{20}$ n-alkyl groups attached to the oxygen atom through a primary or secondary carbon atom, n is a number from 5 to 25, inclusive, and $R_2$ may be an n-alkyl group containing from 1 to 5 carbon atoms. These compositions do not teach or encompass the the claimed compositions.

OBJECTS AND SUMMARY OF THE INVENTION

It is an object of this invention to provide a novel, self-emulsifying alkoxylate ester.

It is still a further object of this invention to provide a method of preventing chalking of antiperspirant compositions containing volatile silicone oil.

It is a further object of this invention to provide a composition useful as a surfactant having both emulsifying and emollient properties for a broad range of cosmetic compositions.

The present invention is broadly directed to a novel, self-emulsifing alkoxylate ester having the structural formula:

wherein, $R_1$ contains from 2 to 20 carbon atoms and is selected from the group consisting of aliphatic and aromatic substituents, $R_3$ is an alkyl or aryl substituent from 1 to 21 carbon atoms, wherein one of $R_1$ and $R_3$ must contain greater than 8 carbon atoms;

$R_2$ is:

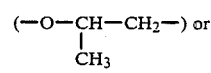 (a)

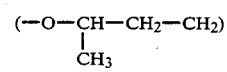 (b)

x is from 1 to 10;
y is from 1 to 20; and
the ratio of y to x is from 2:1 to 10:1.

This invention is further directed to a method of preventing chalking of antiperspirant compositions containing volatile silicone oil comprising adding to the antiperspirant composition a chalking preventative amount of the aforementioned self-emulsifing alkoxylate ester.

This invention is further directed to a composition comprising an emulsion of an internal phase of the alkoxylate ester in a continuous water phase.

DETAILED DESCRIPTION OF THE INVENTION

The alkoxylate esters of the invention, which have the structural formula indicated above, are prepared by initially reacting, either sequentially or in their mixed forms, primary or secondary mono-or polyhydric alkanols, containing from 2 to 20 carbon atoms, including aromatic alcohols, e.g. substituted phenols, diols and glycerine, or other alkoxylatable compounds, e.g. fatty acids, fatty amides, fatty amines, with ethylene oxide, and propylene and/or butylene oxide in the presence of an acidic or basic catalyst. It is typical of propylene and butylene oxide to branch upon opening of the epoxide ring (to form $R_2$, e.g. (a) or (b) in above formula). This branching of $R_2$ tends to impart liquidity to the compound. Catalysts suitable for this reaction are well known in the art and include, for example, inorganic alkalis such as alkali metal oxides and hydroxides, e.g. potassium hydroxide, sodium methoxide, sodium borohydride; normal and Lewis acids, e.g. boron trifluoride, stannic chloride, and sulphuric acid. Amines, quaternary ammonium compounds, water and other acids may also be employed. Mixtures of catalysts may also be employed. Certain reactive substrates known in the art, for example acetylenic alkanols, may obviate the need for such catalysts. Preferably, a basic catalyst is used in this reaction and most preferably from about 0.1 to about 2.0 weight percent of potassium or sodium hydroxide, sodium methoxide, sodium borohydride or mixtures thereof, based on the weight of the alcohol. The reaction is carried out under anhydrous conditions to avoid formation of by-products, and at a temperature which is, preferably, in the range of from about 110° C. to about 200° C., although higher temperatures may be utilized. The reaction may be carried out at substantially atmospheric pressure, although it is preferably carried out in an autoclave at pressures of from about 10 psig to about 80 psig. The amount of ethylene oxide, propylene oxide, and/or butyleneoxide introduced to the reaction zone, and the duration of reaction time, determines the number of moles of such components added to the $R_1$ substituent. Preferably, the reaction is carried out sequentially in that the alcohol (or other alkoylatable compound) is first reacted with the propylene or butylene oxide and after complete reaction, the ethylene oxide is introduced into the reaction. After complete reaction of the ethylene oxide, the reaction mixture, an acid, e.g. phosphoric acid or acetic acid, is introduced into the reaction mixture to neutralize the basic catalyst.

The resultant alkoxylate is then capped with a suitable acyl or aryl group by reacting the alkoxylate with $C_1$-$C_{21}$ alkanoic or aromatic acids, or the acyl or aryl halides or anhydrides of such acids. Preferred acylating reagents include butyric anhydride, acetic anhydride, and stearoyl chloride. Other suitable acids include formic, acetic, benzoic, propanoic, butyric, pentanoic, and hexanoic acids, and the typical halides and anhydrides thereof, including acetyl chloride and acetic anhydride. A conventional esterification reaction of the acid, or acid derivative with the alkoxylate is carried out. This may be accomplished with or without a catalyst. Preferred catalysts are anhydrous methane sulfonic acid and para-toluene sulfonic acid.

As previously indicated, the alkyl group ($R_1$) in the above structural formula contains from 2 to 20 carbon atoms, and is thus preferably derived from alcohols ranging from ethanol to eicosanol. Preferably, the alkyl group ($R_1$) contains from 8 to 18 carbon atoms, depending, however, to some extent, upon the character of the remaining portion of the molecule. The alkoxylate ester may very conveniently contain a mixture derived from the ethoxylation and the propoxolation and/or butoxylation of mixtures of $C_8$ to $C_{18}$ alkanols of even carbon number, since alcohol mixtures of this type are readily available starting materials, for example, the cetostearyl alcohol blends of natural or synthetic origin which are available from several manufacturers, or of mixtures of $C_8$ to $C_{18}$ alkanols of both even and odd carbon numbers, e.g. the NEODOL alcohols of Shell Chemical Co.

The number of moles of propylene oxide or butylene oxide (designated x in the structural formula) and the number of moles of ethylene oxide (designated y in the structural formula) which are incorporated in the alkoxylate ester can range, respectively from 1 to 10 moles and from 1 to 20 moles. The ratio of y to x is from 2:1 to 10:1. The variation of x and y between these ratios can vary the texture and feel of the compound from a silkiness or oily type compound (low y/x ratio) to a dry feeling type compound (high y/x ratio). Other properties are also varied, such as "milkiness" (dispersion quality), water rinsability and cloud points.

In order to achieve the desirable degree of water dispersability in the alkoxylate ester, it is preferred either that the carboxyl group of the compound ($R_3$) or the acyl or aryl group ($R_1$) should contain less than 8 carbon atoms, and preferably 3 or 4 carbon atoms. In order to insure that the compound is not completely water soluble and can perform its surfactant function, the other substituent ($R_1$ or $R_3$) should have greater than 8 carbon atoms therein, preferably from 16 to 18 carbon atoms. The overall molecular structure which is most suitable for the alkoxylate ester of this invention is dictated by the interaction of the several functional groups in the molecule, and the effect of each group on such properties as water dispersability, product color, emulsifiability, cloud point, etc. With respect to liquidity, it is desirable that the alkoxylate ester have a cloud point of less than 15° C. and most preferably less than 0° C. to provide for ease of formulation into products and quality control. The lengthening of the $R_1$ or $R_3$ chain decreases liquidity, especially for straight chain substituents ($R_1$, $R_3$), whereas increasing the number of butoxylate and/or propoxylate groups in the molecule increases liquidity.

The compounds of this invention have unique properties. One substantial property is that they are self-emulsifying, that is 5% to 25% of the compound disperses or "blooms" very easily in water to form a discontinuous phase of the alkoxylate ester in a continuous aqueous phase. By this it is meant that it turns milky white without heating or excessive agitation in water, producing a dispersion of the compound, the particles therein having diameters of 1 to 5 microns. A simple test to determine if a compound is self emulsifying at room temperature (20° C. to 30° C.) is to take 5 ml to 10 ml of the compound to be tested and "float" it on top of 90-95 ml of deionized water which is in a 100 ml graduated cylinder. Cover the top of the cylinder and invert several times. If a milky white emulsion results it is considered to be self emulsifying.

Additionally, the compounds of this invention are particularly useful in preventing the chalking of antiperspirant compositions containing volatile silicone oil. Typically, these antiperspirant compositions are intended to be dispensed in liquid dispersion form, for example, a roller (ball) or stick form. Such antiperspirants are sold by Gillette under the trademark DRY IDEA.

Such antiperspirant compositions suffer from the disadvantage in that when they are applied to the skin and the volatile silicone oil, e.g. polydimethyl siloxane, evaporates, an undesirable white chalky substance is left behind. It has been demonstrated that this white chalky substance is the active antiperspirant ingredient as well as other ingredients used in the antiperspirant composition.

The typical polydimethyl siloxanes that are used in such compositions are volatile in that they will evaporate rapidly from a thin film of the material at body temperature. Such polydimethyl siloxanes are well known in the art, see for example, those described in U.S. Pat. No. 4,264,586 to Callingham et al, the entire disclosure of which is incorporated herein by reference. The proportion of polydimethyl siloxane typically incorporated in such antiperspirant compositions is from about 10% to about 80% by weight of the composition, preferably from 40% to 60% by weight.

There are numerous antiperspirant agents that are used in such antiperspirant compositions such as astringent metal salts, especially aluminum salts. A preferred aluminum salt is aluminum chlorhydrate. Other suitable astringent metal salts include those of zirconium. Further examples are aluminum chlorhydrate, aluminum sulfate, aluminum oxychloride, aluminum oxysulfate, and zirconium hydroxychloride. Other type antiperspirant agents well known in the art may also be used. Other compositions which may be included in the antiperspirant composition are emulsifiers, suspending agents, waxes, water, etc., which are typically found in such compositions.

Upon the addition of the compositions of this invention to such antiperspirant compositions, it has been noted that chalking is prevented upon evaporation of the polydimethyl siloxane from the composition. The amount of compound of this invention added to the antiperspirant composition is preferably at least 3% most preferably 5% to about 10% by weight of the composition to a maximum of about 20%. The upper limit is not critical, in that a minimum amount of the ester should be used to avoid excessive costs and interference with the efficacy of the antiperspirant agent and/or product. To the best of Applicants' knowledge, the use of the compositions of this invention in such antiperspirant compositions does not effect the efficacy thereof.

Additionally, the alkyoxylate esters of this invention have a broad range of usefulness due to the fact that they are self emulsifying and have additional properties which make them useful, for example, certain derivatives of this invention form a stable, non-separating emulsion when added to water. Additionally, stable cosmetic oil-in-water emulsions can be formed at, 25° C. without the usual heating and homogenization. Additional properties are:
1. Unique emolliency;
2. Low cloud point and pour point;
3. Bland odor; and
4. Low toxicity.

The compositions of this invention are thus useful in a broad range of cosmetic compositions. By the use of the term "cosmetic composition", it is meant compositions which are applied to the skin or hair, which are softening or soothing to the skin, and additionally have a cosmetic effect on the skin, e.g., cleansing, odor reducing, odor enhancing, sunshielding, hair or skin softening, lubricating, etc.

Such cosmetic compositions include:
(1) hand cleaners;
(2) bath compositions;
(3) suntan oils and sunscreen butters;
(4) antiperspirant compositions;
(5) perfumes and colognes;
(6) cold creams;
(7) electric preshaves;
(8) eye and throat oils;
(9) skin gels;
(10) topical pharmaceutical ointments;
(11) deodorants;
(12) lotions;
(13) skin moisturizers;
(14) facial cleansers;
(15) cleansing creams;
(16) afer-bath splashes;
(17) hair conditioners;
(18) hair dressings; and
(19) shampoos.

The foregoing list is only exemplary of the type of cosmetic compositions in which the alkoxylate esters may be used and, as such, is not to be considered limiting.

Such compositions may be in the following forms:
(1) anhydrous or aqueous, i.e., oils, solutions, emulsions;
(2) clear or opaque;
(3) creams;
(4) gels;
(5) solids;
(6) sprays; and
(7) foams.

Exemplary classes of cosmetic ingredients and additives which may be used in such skin care compositions are:
(1) emollients;
(2) detergent and emulsifier intermediates;
(3) emulsifiers;
(4) humectants;
(5) antioxidants;
(6) softeners and lubricants;
(7) penetrants, plasticizers, and co-solvents;
(8) sunscreening agents;
(9) suspending and dispersing agents;
(10) antiperspirants;
(11) conditioners;
(12) thickening agents;
(13) preservatives;
(14) antimicrobial agents;
(15) buffers;
(16) chelating agents;
(17) foaming boosters;
(18) foam stabilizers;
(19) coupling agents;
(20) perfumes; and
(21) moisturizers.

Typical cosmetic ingredients and additives that can be used with this invention are:

| Class of Cosmetic Ingredient | Ingredient |
| --- | --- |
| acids | lactic, stearic |
| alkanolamide, foam boosting and foam stability | HETAMIDE LML |
| antimicrobial agent | Triclosan |
| antioxidant | BHA |
| antioxidant | propyl gallate |
| antiperspirant | aluminum and zirconium chlorohydrate |
| buffer | borax |
| chelating agent | Disodium ETA and its salts |
| hair conditioning agent | stearalkonium chloride |
| detergent | cocylsarcosinate, sodium lauryl sulfate |
| emollient (lipophilic) | Isopropyl myristate (IPM) |
| emollient (lipophilic) | Isopropyl palmitate (IPP) |
| emollient (lipophilic) | mineral oil |
| emollient (lipophilic) | silicone oil |
| emollient (lipophilic) | phenyl dimethicone |
| emollient (lipophilic) | cetyl palmitate |
| emulsifier | Glyceryl monostearate (GMS) |
| emulsifier | Sorbitan oleate |
| emulsifying agent | polysorbate 60 (Tween 60) |
| emulsifier | Oleth-2 |
| formation of a TEA stearate soap, an emulsifier | stearic acid and triethanolamine |
| humectant | glycerine |
| humectant | propylene glycol |
| humectant | Sorbitol |
| preservative | methylparaben |
| preservative | propylparaben |
| preservative | quaterium-15 (Dowcil 200) |
| preservative | Glydant (DMDM Hydantoin) |
| sunscreen agent | PARSOL MCX |
| suspending and dispersing agent | Bentone 38 |
| suspending and thickening agent | magnesium aluminum stearate (Veegum) |
| thickening agent | hydroxy propyl cellulose |
| thickening agent | Carbopols, 934, 940, and 941 (carboxy vinyl polymers) |
| wax (lipophilic) | beeswax |
| wax (lipophilic) | paraffin wax |

The amount of alkoxylate ester used in a cosmetic composition is dependent on the type composition, the type and quantity of other cosmetic ingredients used and the amount and type of functional additives. Typically the amount ranges from about 0.5% to about 80%, by weight, of the cosmetic composition. For example, a facial cream may only have about 0.5%, whereas a massage oil may have up to about 80%, by weight. Still higher amounts may be used in, for example bath oils, e.g. 95%.

The following Examples are given to further illustrate the present invention. It is to be understood, however, that the invention is not to be limited thereto.

EXAMPLE 1

Step 1:

791 grams of isoacetyl ($C_{16}$) alcohol, having a molecular weight of 273.9, are charged to a laboratory autoclave. 4 grams of powdered potassium hydroxide catalyst are added, and the autoclave is purged with nitrogen. The autoclave is then heated to 160°–170° C. and 168 grams (2.89 moles) of propylene oxide are introduced at such a rate that a pressure of 50 psi is maintained. After all the propylene oxide is reacted, 282 grams (8.67 moles) of ethylene oxide are introduced at such a rate that a pressure of 50 psi is maintained. After all the ethylene oxide is reacted, the autoclave is cooled and sufficient phosphoric acid is introduced to neutralize the alkaline catalyst to a pH of 5 to 7. The resultant alkoxylate is a pale, oily yellow liquid having a molecular weight of about 464.

Step 2:

To the 1,325 grams (2.85 moles) of the alkoxylate from Step 1 remaining in the autoclave are added 2 grams of anhydrous methane sulfonic acid as an esterification catalyst. The reaction mixture is then agitated and heated to 130°–140° C. under a nitrogen blanket. 473 grams (2.99 moles) of butyric anhydride are introduced at such a rate that 130°–140° C. is maintained. When all the butyric anhydride has been added, the reaction mass is held at 130°–140° C. for 2 hours to assure complete reaction. The batch is then cooled to under 100° C. and washed repeatedly with 10% sodium hydroxide solution until a product of pH of 6 to 7 is achieved. The product is then dried under vacuum and polish filtered. The resultant self-emulsifing alkoxylate ester is a pale yellow liquid having a saponification value of 105.7, an acid value of 0.03, a moisture content of 0.07%, a cloud point of less than $-50\%C$ and a residual hydroxyl number of 3.4, the latter indicating essentially complete esterification. The compound "blooms" or self-emulsifies easily in water.

The following test was performed on a silicone oil containig antiperspirant composition: 10 parts of the above produced compound was added to 90 parts of Gillette DRY IDEA. The compositions were thoroughly mixed and the liquid (about 0.5 grams) applied to a hand. Adjacent to the area, an equal amount of DRY IDEA was applied. The hand was dried. After 5 to 10 minutes the DRY IDEA area was chalky white and the admixture with the compound herein was clear.

It is believed that the compound herein had the following formula:

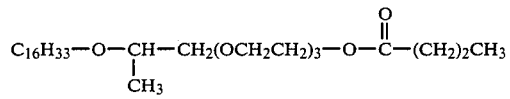

Proposed CTFA* name: PPG-1 Hexadeceth-3 Butyrate.

*Cosmetic, Toiletry and Fragrance Association

EXAMPLE 2

Step 1:

637 grams (2.91 moles) of $C_{14}$–$C_{15}$ alcohols, being primary alcohols which are predominantly linear and produced by the "Shell Process" and are sold under the trademark of "Neodol 45", having an average molecular weight of 219, are charged to a laboratory autoclave. 4 grams of sodium methoxide and 0.5 gram of sodium borohydride are added as catalysts, and the autoclave is evacuated and purged with nitrogen. The autoclave is then heated to 140°–150° C., and 533 grams of a preformed mixture of propylene oxide and ethylene oxide, in a mole ratio of one to three, are introduced at such a rate that a pressure of 25–30 psi is maintained. After all of the mixed alkylene oxides are reacted, the autoclave is cooled and sufficient acetic acid is introduced to neutralize the alkaline catalysts to a pH of 5 to 7. The resultant alkoxylate is a water-white, oily liquid having an average molecular weight of 374.

Step 2:

To the 1,168 grams (3.12 moles) of the alkoxylate from Step 1 remaining in the autoclave are added 2 grams of para toluene sulfonic acid as an esterification catalyst. The reaction mixture is then agitated and heated to 110°–120° C. under a nitrogen blanket. 334 grams (3.27 moles) of acetic anhydride are introduced at such a rate that 110°–120° C. is maintained with external cooling applied. When all the acetic anhydride has been added, the reaction mass is held for 4 hours at reaction temperature to assure complete esterification. The batch is then cooled to 70°–80° C. and washed repeatedly with water to remove the by-product acetic acid, followed by washes with 5% sodium carbonate solution until a product pH of 6 to 7 is achieved. The product is then dried under a vacuum and polish filtered. The resultant alkoxylate ester is a water-white, easily self-emulsifing or "blooming" liquid having a saponification value of 103.3, an acid value of 0.07, a cloud point of less than 0° C., a moisture content of 0.04%, and a residual hydroxyl number of 1.6, the latter indicating complete esterification.

The same test was performed on a silicone oil containing antiperspirant composition as in Example 1 with the same results.

It is believed that the compound produced herein had the following formula:

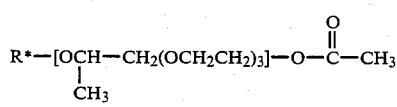

*where R = $C_{14}$–$C_{15}$ Alcohols
Proposed CTFA name: PPG-1 Myreth-3 Acetate.

EXAMPLE 3

Step 1:

263 grams (4.38 moles) of isopropanol are charged to an autoclave. 3.8 grams of powdered potassium hydroxide and 0.3 gram of sodium borohydride are added as catalysts. The autoclave is then purged with nitrogen and heated to 110°–120° C. 193 grams (4.38 moles) of ethylene oxide are introduced at such a rate that 50 psi pressure is maintained. After the ethylene oxide is reacted, the temperature is raised to 160°–170° C. and 737 grams of a preformed mixture of propylene oxide and ethylene oxide in a mole ratio of 1 to 2.5 is introduced at such a rate that a pressure of 40 psi is maintained. After all of the mixed alkylene oxides have reacted, the autoclave is cooled and sufficient phosphoric acid is introduced to neutralize the alkaline catalyst to a pH of 5 to 7. The resultant alkoxylate is a pale yellow, mobile liquid having a molecular weight of about 272.

Step 2:

500 grams (1.84 moles) of the alkoxylate from Step 1 are charged to a 2 liter borosilicate glass reactor fitted with a mechanical agitator, nitrogen sparge, and gas absorption train. The batch is heated to 120°–130° C., and 579 grams (1.9 moles) of stearoyl ($C_{18}$) chloride are introduced at such a rate that the by-product hydrogen chloride is scrubbed completely by the gas absorption train. The batch is then maintained at a temperature of 120°–130° C. and sparged with nitrogen until all but the last traces of hydrogen chloride are removed. The reaction mixture is then cooled to 70°–80° C. and neutralized to a pH of 5 to 6 with sodium hydroxide. The residual salts are removed by filtration.

The resultant easily self-emulsifing alkoxylate ester is a pale yellow liquid having a saponification number of 114.5, an acid value of 1.6, a moisture content of 0.46%, a cloud point of less than 0° C., and a residual hydroxyl value of 5.4.

It is believed that the compound produced herein had the following formula:

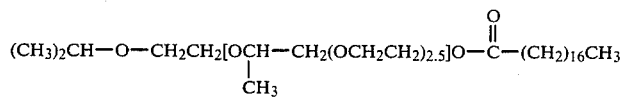

Proposed CTFA name: PPG-1 Isopropeth-3 Stearate

EXAMPLE 4

Step 1:

558 grams (2.0 moles) of Stearamide MEA, made by reacting equimolar amounts of methyl stearate and monoethanolamine using standard catalysts and reaction conditions, are charged to a laboratory autoclave. 4.7 grams of sodium methoxide are added as a catalyst, and the autoclave is evacuated and purged with nitrogen. The autoclave is then heated to 160°–170° C., and 264.3 grams (6.0 moles) of ethylene oxide are introduced at such a rate that a pressure of 50 psi is maintained. After all the ethylene oxide is reacted, 116.2 grams (2.0 moles) of propylene oxide are introduced at such a rate that a pressure of 50 psi is maintained. After all the propylene oxide is reacted, the autoclave is cooled and sufficient glacial acetic acid is introduced to neutralize the alkaline catalyst to a pH of 5 to 7. The resultant alkoxylate is a pale, oily yellow liquid having an average molecular weight of approximately 469.

Step 2:

To the 938 grams (2.0 moles) of the alkoxylated alkanolamide from Step 1 are added 2 grams of anhydrous methane sulfonic acid as an esterification catalyst. The reaction mixture is then agitated and heated to 110°–120° C. under a nitrogen blanket. 214.2 grams (2.1 moles) of acetic anhydride are introduced at such a rate that a temperature of 110°–120° C. is maintained with external cooling applied. When all the acetic anhydride has been added, the reaction mass is held for 4 hours at reaction temperature to assure complete esterification. The batch is then cooled to 70°–80° C. and washed repeatedly with water to remove by-product acetic acid, followed by washes with a 5% sodium carbonate solution until a product pH of 6 to 7 is achieved. The product is then dried under vacuum and polish filtered. The resultant alkoxylate ester is a pale yellow, "blooming" liquid having a saponification value of 218.4, an acid value of 0.42, a cloud point of <0° C., a moisture content of 0.07%, and a residual hydroxyl number of 2.9, the latter indicating essentially complete esterification. It is believed that the compound produced herein has the following formula:

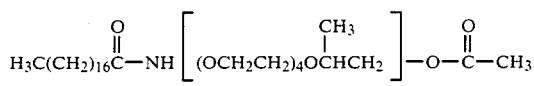

Proposed CTFA name: PPG-1 PEG-4 Stearamide Acetate

EXAMPLE 5

Step 1:

500 grams of triple-pressed stearic acid, having an average molecular weight of 269.8, are charged to a laboratory autoclave. 4.3 grams of powdered potassium hydroxide and 0.4 gram of sodium borohydride are added as catalysts, and the autoclave is heated, evacuated, and purged with nitrogen. At a temperature of 150°–160° C., a pre-formed mixture of 107.6 grams (1.85 moles) of propylene oxide and 245 grams (5.57 moles) of ethylene oxide is introduced at such a rate that a pressure of 40 psi is maintained. After all of the mixed alkylene oxides are reacted, the autoclave is cooled and sufficient phosphoric acid is introduced to neutralize the alkaline catalysts to a pH of 5 to 7. The resultant propylene glycol polyethylene glycol monoester is a white, soft semi-solid having an average molecular weight of about 460, as indicated by its saponification value of 122.1 and hydroxyl number of 125.6.

Step 2:

To the 830 grams (1.8 moles) of the alkoxylate remaining in the autoclave from Step 1 are added 1.5 grams of anhydrous methane sulfonic acid as an esterification catalyst. The reaction mixture is then heated to 120°–130° C. under a nitrogen blanket. The reaction mixture is then agitated and 246 grams (1.89 moles) of propionic anhydride are introduced at such a rate that a temperature of 120°–130° C. is maintained with external cooling applied. When all of the propionic anhydride has been added, the reaction mass is held for 4 hours at reaction temperature to assure complete esterification. The batch is then cooled to 60°–70° C. and washed repeatedly with water to remove the by-product propionic acid, followed by washes with 5% sodium carbonate solution until a product pH of 5 to 6 is achieved. The product is then dried under vacuum and polish filtered. The resultant alkoxylate diester is a pale yellow, self-emulsifying liquid having a saponification value of 217.5, an acid value of 1.2, a moisture content of 0.11%, and a residual hydroxyl number of 0.9, the latter indicating complete esterification. It is believed that the compound produced herein has the following formula:

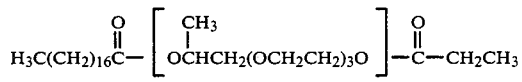

Proposed CTFA name: PPG-1 PEG-3 Stearate Propionate

EXAMPLE 6

Step 1:

725 grams (2.84 moles) of cetyl alcohol are charged to laboratory autoclave. 3.5 grams of sodium methoxide and 0.5 grams of sodium borohydride are added as catalysts, and the autoclave is evacuated and purged with nitrogen. The autoclave is agitated and heated to 140°–150° C., and 539 grams of a preformed mixture of propylene oxide and ethylene oxide, in a mole ratio of one to three, are introduced at such a rate that a pressure of 40-50 psi is maintained. After all of the mixed alkylene oxides are reacted, the autoclave is cooled and sufficient acetic acid is introduced to neutralize the alkaline catalysts to a pH of 5 to 7. The resultant alkoxylate is a water-white, oily liquid having an average molecular weight of about 445.

Step 2:

To the 1,221 grams (2.74 moles) of the alkoxylate from Step 1 remaining in the autoclave are added 1.5 grams of anhydrous methane sulfonic acid as an esterification catalyst. The reaction mixture is then agitated and heated to 110°–120° C. under a nitrogen blanket. 293 grams (2.87 moles) of acetic anhydride are introduced at such a rate that 110°–120° C. is maintained with external cooling applied. When all the acetic anhydride has been added, the reaction mass is held for 4 hours at reaction temperature to assure complete esterification. The batch is then cooled to 70°–80° C., and washed repeatedly with water to remove by-product acetic acid. When an acid number of 5 or less is achieved, 5 grams of a 50% solution of hydrogen peroxide are introduced as a bleach and the batch is agitated for 30 minutes. Next, the batch is washed with portions of 5% sodium carbonate solution until a product pH of 6 to 7 is obtained. The product is then dried under vacuum and polish filtered. The resultant alkoxylate ester is a water-white, readily self-emulsifying or "blooming" liquid having a saponification value of 114.9, an acid value of 0.03, a cloud point less than 15° C., a moisture content of 0.04%, and a residual hydroxyl number of 1.3, the latter indicating complete esterification. An aqueous dispersion at room temperature of this product at a concentration of 10% to 20% forms a stable white emulsion.

It is believed that the compound produced herein has the following formula:

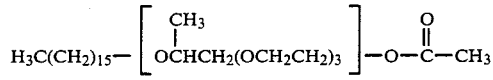

Hetester PCA; PROPOSED-CTFA Nomenclature: PPG-1 Ceteth-3 Acetate

EXAMPLE 7

Step 1:

320.6 grams (1.0 mole) of behenyl alcohol are charged to a laboratory autoclave. 4.2 grams of powdered potassium hydroxide and 0.5 grams of sodium borohydride are added as catalysts, and the autoclave is evacuated and purged with nitrogen. The autoclave is then agitated and heated to 150°–160° C., and 264.3 grams (6.0 moles) of ethylene oxide are introduced at such a rate that a pressure of 50 psi is maintained. Once all of the ethylene oxide is reacted, 174.2 grams (3.0 moles) of propylene oxide are introduced at such a rate that a pressure of 50 psi is maintained. After all of the propylene oxide is reacted, the autoclave is cooled and sufficient acetic acid is introduced to neutralize the alkaline catalysts to a pH of 5 to 7. The resultant alkoxylate is a pale, oily yellow liquid having an average molecular weight of about 670.

Step 2:

To the 724 grams (0.95 mole) of the alkoxylate from Step 1 remaining in the autoclave are added 1.6 grams of anhydrous methane sulfonic acid as an esterification catalyst. The reaction mixture is then agitated and heated to 110°-120° C. under a nitrogen blanket. 102 grams (1.0 mole) of acetic anhydride are introduced at such a rate that 110°-120° C. is maintained. After addition of the acetic anhydride, the reaction mass is held at 110°-120° C. for 4 hours to assure complete esterification. The batch is then cooled to 70°-80° C. and washed repeatedly with water to remove the by-product acetic acid, followed by washes with 5% sodium carbonate solution until a product pH of 6 to 7 is achieved. The product is then dried under vacuum and polish filtered. The resultant alkoxylate ester is an oily yellow liquid which easily self-emulsifies in water, having a saponification value of 70.4, a cloud point of 18° C., a moisture content of 0.11%, and a residual hydroxyl number of 0.3.

It is believed that the compound produced herein has the following formula:

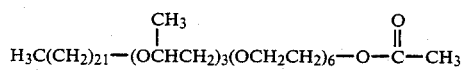

Suggested PROPOSED-CTFA nomenclature PPG-3 Beheneth-6 Acetate.

EXAMPLE 8

Step 1:

840 grams of isocetyl (C16) alcohol, having an average molecular weight of 267.7, are charged to a laboratory autoclave. 4.0 grams of powdered potassium hydroxide and 0.5 grams of sodium borohydride are added as catalysts. The autoclave is then evacuated and purged with nitrogen, agitated and heated to 160°-170° C. 597 grams of a pre-formed mixture of propylene oxide and ethylene oxide, in a mole ratio of one to three, are introduced at such a rate that a pressure of 50 psi is maintained. After all of the mixed alkylene oxides are reacted, the autoclave is cooled and sufficient lactic acid is introduced to neutralize the alkaline catalysts to a pH of 5 to 7. The resultant alkoxylate is a water-white, oily liquid having an average molecular weight of about 458.

Step 2:

1,400 grams (3.06 moles) of the alkoxylate from Step 1 are charged to a 3 liter borosilicate glass reactor fitted with a mechanical agitator, nitrogen sparge and gas absorption train. The batch is agitated and heated to 120°-130° C., and 426 grams (3.21 moles) of pivaloyl chloride (neo pentanoic acid chloride) are introduced at such a rate that the by-product hydrogen chloride is scrubbed completely by the gas absorption train. The batch is then maintained at a temperature of 120°-130° C. and sparged with nitrogen until all but the last traces of hydrogen chloride are removed. The reaction mixture is then cooled to 70°-80° C. and neutralized to a pH of 5 to 6 with sodium hydroxide. The residual salts are removed by filtration, and the product is washed with portions of 5% sodium carbonate solution until a product pH of 6 to 7 is achieved and all traces of odor attributable to free neopentanoic acid are eliminated. The compound is then dried under vacuum and polish filtered.

The resultant self-emulsifying alkoxylate ester is a pale yellow liquid having a saponification value of 101.7, a nil acid value, a cloud point less than −50° C., a moisture content of 0.05%, and a residual hydroxyl number of 1.1, the latter indicating complete esterification.

It is believed that the compound produced herein has the following formula:

PROPOSED-CTFA Nomenclature: PPG-1 Isoceteth-3 Neopentanoate.

EXAMPLE 9

COSMETIC CREAM

| Oil-In-Water Cream | Ingredient | "Cold Mix" % |
|---|---|---|
| Phase A | Water, deionized | 70.0 |
| | Carbopol 940, 2% aqueous (thickener) | 15.0 |
| Phase B | Water, deionized | 2.7 |
| | Triethanolamine, 99% (alkali) | 0.3 |
| Phase C | PPG-1 Ceteth 3-Acetate (PCA) [Example 6] | 10.0 |
| Phase D | Kathon CG (Preservative) | 0.1 |
| | Water, deionized | 1.9 |
| | | 100.00% TOTAL |

Add B to A, then C, then D. Mix at 25° C. until uniform.

EXAMPLE 10

LOTION

| Oil-In-Water Lotion | Ingredient | "Cold Mix" % |
|---|---|---|
| Phase A | Water, deionized | 87.4 |
| Phase B (dry blend) | Veegum (thickener) | 0.3 |
| | Carbopol 934 | 0.2 |
| Phase C | Water, deionized | 1.8 |
| | Triethanalamine, 99% | 0.2 |
| Phase D | PPG 1 Ceteth 3-Acetate (PCA) [Example 6] | 10.0 |
| Phase E | Kathon CG | 0.1 |
| | | 100.00% TOTAL |

Add B slowly to A with good mixing at 25° C. When smooth, add C, then D, then E. Mix until uniform.

EXAMPLE 11

DISPERSIBLE BATH OIL

| Oil-In-Water Bath Oil | Ingredient | "Cold Mix" % |
|---|---|---|
| | Bernel Ester DOM (dioctyl maleate) | 50.0 |
| | PPG 1 Hedadeceth 3-Butyrate (PHB) | 50.0 |
| | Perfume | Q.S. |

| Oil-In-Water Bath Oil | Ingredient | "Cold Mix" % |
|---|---|---|
| | | 100.00% TOTAL |

EXAMPLE 12

PIGMENTED LOTION

| Oil-In-Water Lotion | Ingredient | "Cold Mix" % |
|---|---|---|
| Phase A | Water, deionized | 73.15 |
| Phase B | CMC 7MF | 0.50 |
| (dry blend) | Veegum (thickeners) | 1.25 |
| Phase C | Kathon CG | 0.10 |
| Phase D | Hetester PCA PPG 1 Ceteth 3-Acetate [Example 6] | 15.00 |
| Phase E (micro-pulverized) | Pigment blend | 10.00* |
| | | 100.00% TOTAL |

| *TiO₂ | #3328 - (WC&D) | 6.80 Parts |
|---|---|---|
| Yellow | 7055 - (WC&D) | 1.15 |
| Red | 7054 - (WC&D) | 0.40 |
| Black | C-33-134 (Sun) | 0.15 |
| Talc | 141 (WC&D) | 1.50 |
| | | 10.00 Parts Total |

Add B to A, mix until smooth, then C, then D, mix well, then E, mix until smooth.

The invention has been described with respect to illustrations and working examples thereof but is not to be considered as limited to them because it is evident that one of skill in the art with the present specification before him will be able to utilize substitutes and equivalents without departing from the spirit and scope of the invention.

What is claimed is:

1. A self-emulsifying alkoxylate ester having a structural formula:

$$R_1-(R_2)_x-(O-CH_2-CH_2)_y-O-\overset{O}{\underset{\|}{C}}-R_3$$

wherein:
R₁ contains from 2 to 20 carbon atoms and is selected from the group consisting of aliphatic and aromatic substituents;
R₃ is an alkyl or aryl substituent from 1 to 21 carbon atoms;
one of R₁ and R₃ must contain greater than 8 carbon atoms;
R₂ is:

$$(-O-\underset{\underset{CH_3}{|}}{CH}-CH_2-) \text{ or } (-O-\underset{\underset{CH_3}{|}}{CH}-CH_2-CH_2);$$

x is from 1 to 10;
y is from 1 to 20; and
the ratio of y to x is from 2:1 to 10:1.

2. The ester of claim 1, wherein R₁ plus R₃ contains from 12 to 28 carbon atoms.

3. The ester of claim 1, wherein R₁ plus R₃ contains from 12 to 20 carbon atoms.

4. The ester of claim 1, wherein the ratio of y to x is from 3:1 to 4:1.

5. The ester of claim 2 or 3, wherein the ratio of y to x is from 3:1 to 4:1.

6. The ester of claim 1 or 4, wherein R₁ contains from 16 to 18 carbon atoms and R₃ contains 3 or 4 carbon atoms.

7. The ester of claim 1, 2, 3, or 4, wherein R₂ is:

$$(-O-\underset{\underset{CH_3}{|}}{CH}-CH_2).$$

8. The ester of claim 1, 2, 3, or 4, wherein R₂ is:

$$(-O-\underset{\underset{CH_3}{|}}{CH}-CH_2-CH_2)$$

9. A method of preventing chalking of a liquid dispersion antiperspirant composition containing volatile silicone oil, comprising adding to the antiperspirant composition a chalk preventative amount of a self-emulsifying alokoxylate ester having the structural formula:

$$R_1-(R_2)_x-(O-CH_2-CH_2)_y-O-\overset{O}{\underset{\|}{C}}-R_3$$

wherein:
R₁ contains from 2 to 20 carbon atoms and is selected from the group consisting of aliphatic and aromatic substituents;
R₃ is an alkyl or aryl substituent from 1 to 21 carbon atoms;
one of R₁ and R₃ must contain greater than 8 carbon atoms;
R₂ is:

$$(-O-\underset{\underset{CH_3}{|}}{CH}-CH_2-) \text{ or } (-O-\underset{\underset{CH_3}{|}}{CH}-CH_2-CH_2);$$

x is from 1 to 10;
y is from 1 to 20; and
the ratio of y to x is from 2:1 to 10:1.

10. The method of claim 9, wherein R₁ plus R₃ contains from 12 to 28 carbon atoms.

11. The method of claim 9, wherein R₁ plus R₃ contains from 12 to 20 carbon atoms.

12. The method of claim 9, wherein the ratio of y to x is from 3:1 to 4:1.

13. The method of claim 10 or 11, wherein the ratio of y to x is from 3:1 to 4:1.

14. The method of claim 9 or 12, wherein R₁ contains from 16 to 18 carbon atoms, and R₃ contains 3 or 4 carbon atoms.

15. The method of claim 9, 10, 11 or 12, wherein R₂ is:

$$(-O-\underset{\underset{CH_3}{|}}{CH}-CH_2-).$$

16. The method of claim 9, 10, 11 or 12, wherein R₂ is:

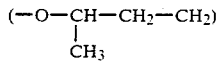

17. The method of claim 9, 10, 11, or 12, wherein the chalking preventative amount is at least about 3% by weight of the antiperspirant composition.

18. A composition comprising an emulsion of an internal phase of the ester of claims 1, 2, 3 or 4, in a continuous water phase.

19. The composition of claim 18, wherein the ester is present in the composition from about 5% to 25% by weight.

20. The composition of claim 18, further comprising a stabilizing amount of a water soluble or dispersible thickener in the continuous water phase.

21. The composition of claim 18, further comprising an amount of a lipophilic ingredient in the internal phase.

22. The composition of claim 18, further comprising a stabilizing amount of a water soluble of dispersible thickener in the continuous phase and an amount of a lipophilic ingredient in the internal phase.

23. A self-emulsifying alkoxylate ester having a structural formula:

$$C_{16}H_{33}-O-\underset{\underset{CH_3}{|}}{CH}-CH_2(OCH_2CH_2)_3-O-\overset{\overset{O}{\|}}{C}-(CH_2)_2CH_3.$$

24. A self-emulsifying alkoxylate ester having a structural formula:

$$R_1-[O\underset{\underset{CH_3}{|}}{CH}-CH_2(OCH_2CH_2)_3]-O-\overset{\overset{O}{\|}}{C}-CH_3$$

wherein $R_1 = C_{14}-C_{15}$.

25. A self-emulsifying alkoxylate ester having a structural formula:

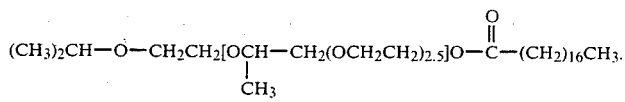

26. A self-emulsifying alkoxylate ester having a structural formula:

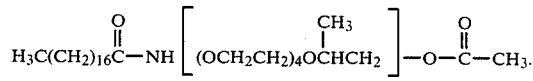

27. A self-emulsifying alkoxylate ester having a structural formula:

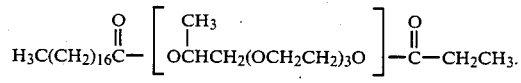

28. A self-emulsifying alkoxylate ester having a structural formula:

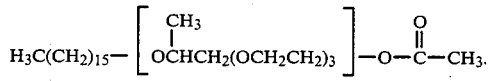

29. A self-emulsifying alkoxylate ester having a structural formula:

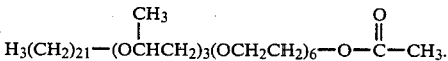

30. A self-emulsifying alkoxylate ester having a structural formula:

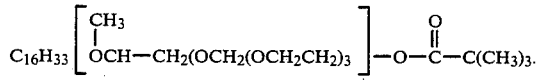

* * * * *